(12) United States Patent
Olbert et al.

(10) Patent No.: US 8,969,644 B2
(45) Date of Patent: Mar. 3, 2015

(54) METHOD FOR PROVIDING AN OXYGEN-CONTAINING GAS STREAM FOR THE ENDOTHERMIC REACTION OF AN INITIAL STREAM COMPRISING ONE OR MORE HYDROCARBONS

(75) Inventors: Gerhard Olbert, Dossenheim (DE); Franz Corr, Ludwigshafen (DE); Sven Crone, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 656 days.

(21) Appl. No.: 12/525,830

(22) PCT Filed: Jan. 31, 2008

(86) PCT No.: PCT/EP2008/051208
§ 371 (c)(1),
(2), (4) Date: Aug. 5, 2009

(87) PCT Pub. No.: WO2008/095860
PCT Pub. Date: Aug. 14, 2008

(65) Prior Publication Data
US 2010/0094071 A1    Apr. 15, 2010

(30) Foreign Application Priority Data

Feb. 6, 2007    (EP) .................................. 07101829

(51) Int. Cl.
*C07C 5/48*    (2006.01)
*F23C 6/04*    (2006.01)
(Continued)

(52) U.S. Cl.
CPC ............ *F23C 6/045* (2013.01); *B01J 4/005* (2013.01); *C01B 3/36* (2013.01); *C07C 5/48* (2013.01);
(Continued)

(58) Field of Classification Search
CPC ............ C07C 5/48; C07C 11/06; F23C 6/045

USPC ............... 48/127.1, 198.1, 127.9; 423/245.3; 585/658, 654, 656, 659; 568/475; 431/10, 11, 12
See application file for complete search history.

(56) References Cited

U.S. PATENT DOCUMENTS 4,474,121 A * 10/1984 Lewis ............................ 110/346
4,761,132 A * 8/1988 Khinkis .......................... 431/10
(Continued)

FOREIGN PATENT DOCUMENTS

EP    0 406 071    1/1991
GB    776 106    6/1957
(Continued)

OTHER PUBLICATIONS

Lide, et al., CRC Handbook of Chemistry and Physics, 91st ed., 2011 Internet edition.*
(Continued)

*Primary Examiner* — In Suk Bullock
*Assistant Examiner* — Bradley Etherton
(74) *Attorney, Agent, or Firm* — Oblon, McClelland, Maier & Neustadt, L.L.P.

(57) ABSTRACT

A method is proposed for providing an oxygen-containing gas stream for the endothermic reaction of an initial stream comprising one or more hydrocarbons, having a predetermined oxygen concentration and a predetermined temperature, wherein a fluid fuel stream
is combusted with a primary air stream at λ values of the primary air stream to the fluid fuel stream of from 0.6 to 1.2 to obtain a combustion gas stream,
and a secondary air stream is admixed to the combustion gas stream to obtain the oxygen-containing gas stream for the endothermic reaction,
with the predetermined oxygen concentration and the predetermined temperature of the oxygen-containing gas stream being adjusted via the flow rate and the temperature of the secondary air stream.

18 Claims, 1 Drawing Sheet

(51) Int. Cl.
*B01J 4/00* (2006.01)
*C01B 3/36* (2006.01)
*F23L 7/00* (2006.01)

(52) U.S. Cl.
CPC ......... *F23L 7/005* (2013.01); *C01B 2203/0255* (2013.01); *F23C 2900/06041* (2013.01); *Y02E 20/344* (2013.01)
USPC ........ 585/658; 48/127.1; 48/127.9; 48/198.1; 431/10; 431/11; 431/12; 585/654; 585/656; 585/659

(56) References Cited

U.S. PATENT DOCUMENTS

| | | | |
|---|---|---|---|
| 5,087,270 | A | 2/1992 | Gateau et al. |
| 5,198,580 | A * | 3/1993 | Bartek et al. ............... 562/542 |
| 5,549,877 | A * | 8/1996 | Gateau et al. ............. 423/245.3 |
| 5,784,876 | A | 7/1998 | Alkabie |
| 5,997,596 | A | 12/1999 | Joshi et al. |
| 6,793,693 | B1 * | 9/2004 | Koehne et al. ................. 44/300 |
| 2002/0050097 | A1 | 5/2002 | Fournier et al. |
| 2002/0055664 | A1 * | 5/2002 | Liu .............................. 585/658 |
| 2004/0199039 | A1 * | 10/2004 | Brophy et al. ............... 585/660 |
| 2005/0119515 | A1 * | 6/2005 | Machhammer et al. ...... 585/658 |
| 2006/0004226 | A1 * | 1/2006 | Machhammer et al. ...... 562/526 |
| 2008/0300440 | A1 * | 12/2008 | Heinritz-Adrian ........... 585/659 |

FOREIGN PATENT DOCUMENTS

| | | |
|---|---|---|
| GB | 1 394 988 | 5/1975 |
| WO | 99/11571 | 3/1999 |
| WO | 00/06948 | 2/2000 |
| WO | WO 2006/050957 A1 * | 5/2006 ............. C07C 5/333 |
| WO | 2006/119812 | 11/2006 |

OTHER PUBLICATIONS

Standard enthalpy of formation data for propane, propene, and water avaialable at www.webbook.nist.gov—accessed Mar. 9, 2014.*

* cited by examiner

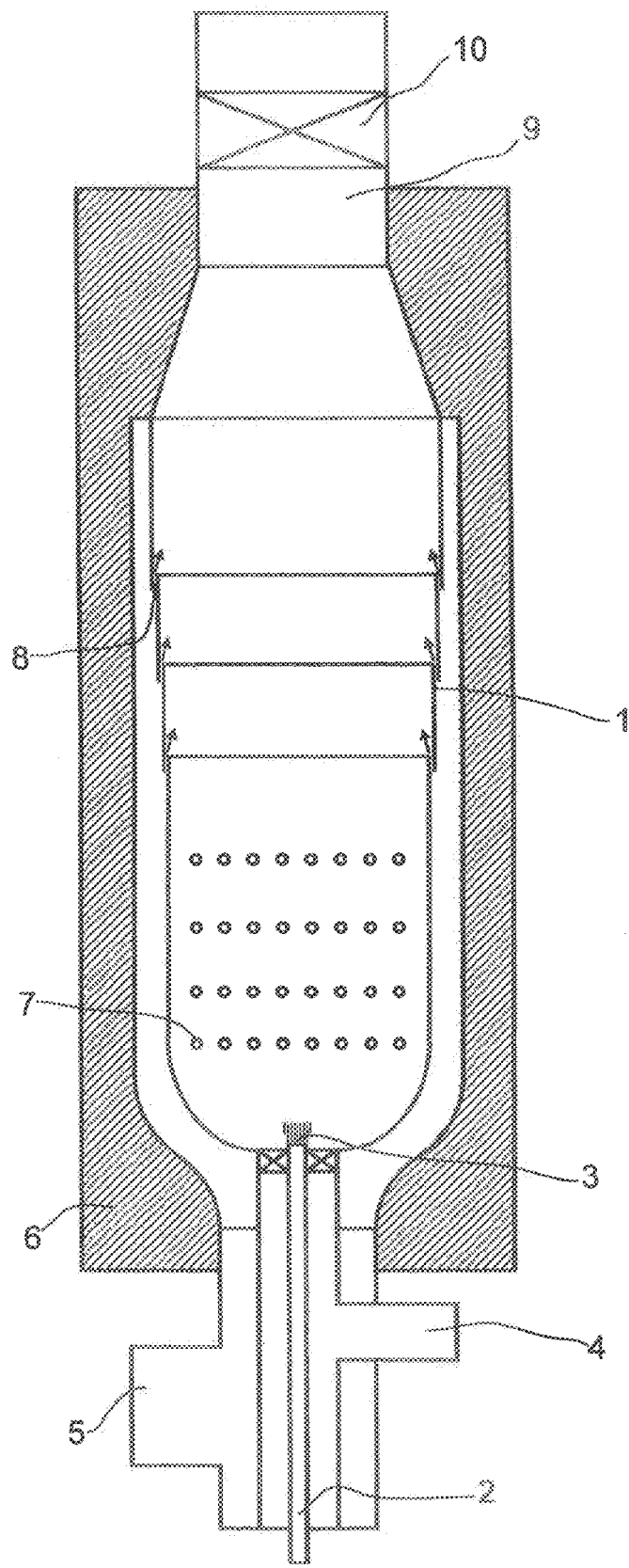

METHOD FOR PROVIDING AN OXYGEN-CONTAINING GAS STREAM FOR THE ENDOTHERMIC REACTION OF AN INITIAL STREAM COMPRISING ONE OR MORE HYDROCARBONS

This application is a 371 of PCT/EP2008/051208, filed Jan. 31, 2008.

The invention relates to a method for providing an oxygen-containing gas stream for the endothermic reaction of an initial stream comprising one or more hydrocarbons, having a predetermined oxygen concentration and a predetermined temperature, a device for carrying out the method and its use.

It is often necessary to provide an oxygen-containing initial stream having a predetermined oxygen concentration and a predetermined temperature for the use in endothermic reaction processes. The required temperatures are often so high that they cannot be attained by heat integration with the process' own product streams alone. For this reason, in processes according to the state of the art, often, the oxygen-containing feed gas stream is electrically heated, which is very costly, especially for large plants. Electric heating has the further disadvantage that it is particularly difficult to regulate.

It was therefore the object of the present invention to provide a method and a device for providing an oxygen-containing feed gas stream having a predetermined oxygen concentration and a predetermined temperature, which can be realized in a technically simple manner and is less costly compared to electric heating, and which enables selective adjustment of the oxygen content and of the temperature.

The object is solved by a method for providing an oxygen-containing gas stream for the endothermic reaction of an initial stream comprising one or more hydrocarbons, having a predetermined oxygen concentration and a predetermined temperature, wherein a fluid fuel stream is combusted with a primary air stream at $\lambda$ values of the primary air stream to the fluid fuel stream of from 0.6 to 1.2 to obtain a combustion gas stream, and a secondary air stream is admixed to the combustion gas stream to obtain the oxygen-containing gas stream for the endothermic reaction, with the predetermined oxygen concentration and the predetermined temperature of the oxygen-containing gas stream being adjusted via the flow rate and the temperature of the secondary air stream.

It has been found that, by combusting a fluid fuel stream with a first, so called primary air stream and subsequent admixing of a further, so called secondary air stream, it is possible to provide a gas stream for the endothermic reaction, which meets the requirements for a predetermined endothermic reaction with respect to the oxygen concentration and with respect to the temperature. The oxygen-containing gas stream provided is a direct oxidant for covering the heat requirements for the predetermined endothermic reaction.

Fluid is taken to mean, as is customary, all liquids, vapors and gases which obey the flow laws of non-solid continua. The fluid fuel stream can be in particular a gaseous fuel stream.

The fluid fuel stream can particularly advantageously be a partial stream of the initial stream which is already present in the plant for the subsequent endothermic reaction process and which comprises one or more hydrocarbons.

Advantageously, the fluid fuel stream, which is a partial stream of the initial stream which is already present in the plant for the subsequent endothermic reaction process and which comprises one or more hydrocarbons, can additionally have a methane-containing gas admixed thereto.

Furthermore, the fluid fuel stream, which is a partial stream of the initial stream for the endothermic reaction containing one or more hydrocarbons, can additionally have a return stream from the endothermic reaction admixed thereto.

The endothermic reaction using an oxygen-containing gas stream can be, for example, an oxydehydration or a partial oxidation.

Accordingly, the initial stream comprises one or more hydrocarbons, which are initial substances for the respective endothermic reaction.

The proportion of the fluid fuel stream to be used in the subsequent endothermic reaction is determined from the concrete requirements of the reaction to be carried out, in particular the temperature that the oxygen-containing gas stream must have during the introduction into the endothermic reaction. This temperature can often be in the range of from 400 to 700° C.

The term $\lambda$ value is used in known manner to characterize mixture compositions comprising one or more fuels, in particular hydrocarbons and air, and is defined as the actual air to fuel ratio, relative to the stoichiometric air to fuel ratio. Consequently, a $\lambda$ value of 1 corresponds to the composition for complete combustion, $\lambda$ values of greater than 1 correspond to lean and $\lambda$ values of less than 1 to rich air/fuel mixtures.

In accordance with the method according to the invention, the $\lambda$ value of the mixture of the fluid fuel stream and the primary air stream is adjusted to a $\lambda$ value in the range of from 0.6 to 1.2, that is, the mixture is adjusted from slightly rich to slightly lean. Accordingly, the combustion gas stream can still comprise residual hydrocarbons. These are, if necessary, completely combusted in the subsequent method step by admixing the secondary air stream. Preferably, the combustion gas stream can, however, also comprise an excess of unused oxygen, in particular in the range of from 2 to 3% by volume, relative to the total volume of the combustion gas stream.

Combustion of the partial stream of the initial stream with the primary air stream takes place in particular at a temperature in the range of from 1500 to 1700° C.

The combustion gas stream has subsequently a secondary air stream admixed thereto, which comprises preferably water vapor in order to suppress soot formation during combustion.

The proportion of the added water vapor in the secondary air stream is preferably selected so that the water vapor content in the discharge gas stream, that is in the oxygen-containing gas stream which is used in the endothermic reaction, is in the range of from 0 to 50% by volume, in particular in the range of from 0.5 to 4% by volume.

Preferably, the primary air stream and the secondary air stream are preheated, in particular to a temperature in the range of from 150 to 200° C., preferably to approximately 170° C.

Preferably, preheating of the primary air stream and/or of the secondary air stream can be carried out by heat integration with the product stream of the endothermic reaction.

The oxygen content of the oxygen-containing stream provided with the method is adjusted, in particular by a corresponding regulation of the added quantity of water steam and in particular secondary air, preferably to a value in the range between 2 and 20% by volume, more preferably between 13 and 20% by volume.

A further object of the invention is a device for carrying out the above method for providing an oxygen-containing gas stream for the endothermic reaction of an initial stream comprising one or more hydrocarbons, having a predetermined oxygen concentration and a predetermined temperature, wherein a fluid fuel stream is completely combusted with a primary air stream at λ values of the fluid fuel stream of from 0.6 to 1.2 to obtain a combustion gas stream, and a secondary air stream is admixed to the combustion gas stream to obtain the oxygen-containing gas stream for the endothermic reaction, with the predetermined oxygen concentration and the predetermined temperature of the oxygen-containing gas stream being adjusted via the flow rate and the temperature of the secondary air stream, the device being characterized by an elongated combustion chamber having a supply of the fluid fuel stream by means of one or more nozzles which are centrally arranged at one end of the combustion chamber to form a burner, and of the primary air stream into the region of the nozzles, a supply of the secondary air stream by means of openings on the perimeter of the combustion chamber, and having an outlet opening for the oxygen-containing gas stream provided by the method at the other end of the combustion chamber.

The device comprises an elongated combustion chamber, which is made of a high temperature resistant material, in particular a high temperature resistant steel, preferably a chromium-nickel steel, and which is provided with an external heat insulation. The combustion chamber can be substantially cuboid. Substantially is herein taken to mean that the geometry of the combustion chamber, in particular at both ends thereof, that is in the region of the supply of the combustion gases to the burner and in the region of the outlet opening, may differ from the cuboid geometry.

The combustion chamber is substantially cylindrical. Substantially is herein taken to mean that the geometry of the combustion chamber, in particular at both ends thereof, that is in the region of the supply of the combustion gases to the burner and in the region of the outlet opening, may differ from the cylindrical geometry. In addition, in a preferred embodiment, the combustion chamber wall is comprised of two or more concentric sections having increasing diameter with increasing distance from the burner end of the combustion chamber, this embodiment thus also being only substantially cylindrical and not exactly cylindrical.

The combustion chamber can be preferably arranged in an upright position, the burner end being at the bottom and the outlet end being at the top.

The elongated combustion chamber has a supply for the fluid fuel stream at one end thereof, said supply being centrally arranged and opening out into the combustion chamber by way of one or more nozzles forming a burner.

The primary air stream is introduced into the region of the nozzles, in particular by means of a line which is concentrically arranged around the supply line for the fluid fuel stream.

The combustion is monitored by means of a flame detector, as it is customary in burner technology.

Openings are provided on the perimeter of the combustion chamber for admixing secondary air to the combustion gases from the burner.

These can be perforations in the combustion chamber wall, which may be arranged in the combustion chamber region following the burner on one or more annular paths along the perimeter.

However, the openings on the perimeter of the combustion chamber for the supply of the secondary air are preferably fin-like annular slots. These are preferably arranged starting from the middle of the combustion chamber and are formed as a result of the combustion chamber wall being comprised of two or more concentric tube sections, the diameter of which increases with increasing distance of the tube sections from the burner, and wherein the outer diameter of the preceding tube section is smaller than the inner diameter of the respective subsequent tube section. As a result, the annular slots for the supply of the secondary air stream remain between the tube sections, which are partly inserted into one another.

By way of the special embodiment having the above described annular slots for the supply of the secondary air stream, not only the adjustment of the predetermined oxygen content and of the predetermined temperature for the oxygen-containing gas stream to be provided is achieved, but the secondary air stream has, in addition, a cooling effect for the combustion chamber wall.

At the end of the combustion chamber, which is opposite the burner, there is an outlet opening for the oxygen-containing gas stream. A static mixer can preferably be disposed in the region of the outlet opening.

The object of the invention is also the use of the previously described method and of the previously described device for providing an oxygen-containing gas stream in oxydehydration processes, in particular in the oxydehydration of propane or in the oxydehydration of butane.

The invention will now be explained in more detail with reference to a drawing.

The only FIG. 1 shows a schematic sectional view through a preferred embodiment for a combustion chamber according to the invention.

At one end, the combustion chamber 1 has a supply 2 for the fluid fuel stream, which ends in one or more nozzles 3 in the combustion chamber 1, and a supply 4 for the primary air stream, which is arranged concentrically around the supply 2 for the initial stream and which opens out in the region of the nozzles 3.

The secondary air stream is conducted into the combustion chamber via a further supply 5 between the outer wall of the combustion chamber 1 and the insulation 6 and can enter the combustion chamber 1 via perforations 7, which are arranged, by way of example, on four annular paths along the perimeter.

Starting from approximately the middle of the combustion chamber 1, three annular slots 8 are provided by way of example, through which the secondary air flows into the combustion chamber 1 along the combustion chamber wall.

The combustion chamber ends in an outlet opening 9 for the oxygen-containing gas stream. A static mixer 10 is disposed in the region of the outlet opening 9.

What is claimed is:

1. A method comprising reacting an initial stream comprising one or more hydrocarbons with an oxygen-containing gas stream, to form a product stream, wherein:

the oxygen-containing gas stream has a predetermined oxygen concentration and a predetermined temperature;

the oxygen-containing gas stream is obtained by combusting a fluid fuel stream with a primary air stream, such that λ values of the primary air stream to the fluid fuel stream range from 0.6 to 1.2, to obtain a combustion gas stream, and then admixing secondary air stream with the combustion gas stream to obtain the oxygen-containing gas stream;

the predetermined oxygen concentration of the oxygen-containing gas stream ranges from 2 to 20 vol. % and the predetermined temperature of the oxygen-containing gas stream is adjusted via flow rate and temperature of the secondary air stream; and the combusting and the admixing occur within a combustion chamber comprising a supply of the fluid fuel stream in the form of at least one burner centrally arranged at one end of the combustion chamber, a supply of the primary air stream in the region of the at least one burner, a supply of the secondary air stream in the form of opening on the perimeter of the combustion chamber, and an outlet for the oxygen-containing gas at the other end of the combustion chamber.

2. The method as claimed in claim 1, wherein the reaction is an oxydehydration of propane or of butane.

3. The method as claimed in claim 1, wherein the secondary air stream comprises water vapor.

4. The method as claimed in claim 3, wherein the water vapor content in the secondary air stream is adjusted such that the oxygen-containing gas stream has a water vapor content ranging from 0 to 50% by volume.

5. The method as claimed in claim 1, wherein the fluid fuel stream is a partial stream of the initial stream comprising the one or more hydrocarbons.

6. The method as claimed in claim 5, wherein the fluid fuel stream further comprises a methane-containing gas admixed thereto.

7. The method as claimed in claim 5, wherein the fluid fuel stream further comprises a return stream from the reaction admixed thereto.

8. The method as claimed in claim 1, wherein the fluid fuel stream is combusted with the primary air stream at a $\lambda$ value of 0.8.

9. The method as claimed in claim 1, wherein at least one of the primary air stream and the secondary air stream are preheated by heat integration with the product stream from the reaction.

10. The method as claimed in claim 9, wherein the preheating of at least one of the primary air stream and the secondary air stream occurs at a temperature of between 150 and 200° C.

11. The method as claimed in claim 1, wherein the combustion gas stream comprises 2 to 3% by volume of residual oxygen.

12. The method as claimed in claim 1, wherein the reaction is a partial oxidation.

13. The method of claim 1, wherein the combustion chamber is an elongated combustion chamber having a geometry which is substantially cuboid or substantially cylindrical.

14. The method of claim 1, wherein the openings for the supply of the secondary air stream are perforations in the combustion chamber wall, which are arranged in the combustion chamber region following the at least one burner on one or more annular paths along the perimeter of the combustion chamber.

15. The method of claim 14, wherein the openings on the perimeter of the combustion chamber are fin-like annular slots.

16. The method of claim 1, wherein the combustion chamber comprises two or more concentric tube sections, the diameter of which increases with increasing distance of the tube sections from the at least one burner.

17. A method comprising reacting an initial stream comprising one or more hydrocarbons with an oxygen-containing gas stream, to form a product stream, wherein:

the oxygen-containing gas stream has a predetermined oxygen concentration and a predetermined temperature;

the oxygen-containing gas stream is obtained by combusting a fluid fuel stream with a primary air stream, such that $\lambda$ values of the primary air stream to the fluid fuel stream are greater than 1.0, to obtain a combustion gas stream, and then admixing secondary air stream with the combustion gas stream to provide the oxygen-containing gas stream; and the predetermined oxygen concentration of the oxygen-containing gas stream ranges from 2 to 20 vol. % and the predetermined temperature of the oxygen-containing gas stream is adjusted via flow rate and temperature of the secondary air stream.

18. The method of claim 17, wherein the combustion gas stream comprises 2 to 3% by volume of residual oxygen.

* * * * *